United States Patent
Guzman et al.

(10) Patent No.: US 10,905,761 B2
(45) Date of Patent: Feb. 2, 2021

(54) USE OF A LIPOPEPTIDE OR LIPOPROTEIN AS AN ADJUVANT IN THERAPEUTIC OR PROPHYLACTIC VACCINATIONS

(71) Applicant: HELMHOLTZ-ZENTRUM FUER INFEKTIONSFORSCHUNG GMBH, Braunschweig (DE)

(72) Inventors: Carlos Alberto Guzman, Wolfenbuttel (DE); Peter Muhlradt, Braunschweig (DE)

(73) Assignee: HELMHOLTZ-ZENTRUM FUER INFEKTIONSFORSCHUNG GMBH, Braunschweig (DE)

(*) Notice: Subject to any disclaimer, the term of this patent is extended or adjusted under 35 U.S.C. 154(b) by 1869 days.

(21) Appl. No.: 13/848,936

(22) Filed: Mar. 22, 2013

(65) Prior Publication Data
US 2016/0256542 A1    Sep. 8, 2016

Related U.S. Application Data

(63) Continuation of application No. 10/509,917, filed as application No. PCT/DE03/03497 on Apr. 3, 2003, now abandoned.

(30) Foreign Application Priority Data

Apr. 4, 2002   (DE) .................................... 02007640

(51) Int. Cl.
A61K 39/39    (2006.01)
A61K 39/00    (2006.01)

(52) U.S. Cl.
CPC ........ *A61K 39/39* (2013.01); *A61K 2039/541* (2013.01)

(58) Field of Classification Search
None
See application file for complete search history.

(56) References Cited

U.S. PATENT DOCUMENTS 6,573,242 B1    6/2003   Muehlradt

FOREIGN PATENT DOCUMENTS

| DE | 196 52 586 A1 | 12/1996 |
| WO | WO 93/22343   | 11/1993 |
| WO | WO 98/27110   |  6/1998 |
| WO | WO 99/59610   | 11/1999 |

OTHER PUBLICATIONS

Foss et al. (Advances in Veterinary Medicine, 1999, vol. 41, pp. 83-104).*
XP-002227431 Shibata et al. "The N-Terminal Lipopeptide of a 44-kDa Membrane-Bound Lipoprotein of Mycoplasma salivariam Is Responsible for the Expression of Intercellular Adhesion Molecule-1 on the Cell Surface of Normal Human Gingival Fibroblasts" The Journal of of Immunology, pp. 6538-6544; Dec. 1, 2000.
XP-002070516 Muhlradt et al. "Identification of S-(2,3 Dihydroxypropl) cystein in a Macrophage-Activating Lipopeptide from Mycoplasma fermentas" American Chemical Society, Biochemistry vol. 35 No. 24; pp. 7781-7786 1996.
XP-002254742 Muhlradt et al. "Structure and Specific Activity of Macrophage-Stimulating Lipopeptides from Mycoplasma hyorhinis" Infecction and Immunity, American Society of Microbiology, vol. 66 No. 10; pp. 4804-4810 1998.
XP002254743 Rharbaoui et al. "The Mycoplasma-derived lipopeptide MALP-2 is a potent mucosal adjuvant" Eur J. Immunol, pp. 2857-2865; 2002.
McGhee et al. "The mucosal immune system: from fundamental concepts to vaccine development" Reviews, Vaccine, vol. 10 Issue 2 1992; pp. 75-88.
Holmgren et al. "Cholera toxin and cholera B subunit as ora-mucosal adjuvant and antigen vector systems" Reviews, Vaccine, vol. 11, Issue 12 1993; pp. 1179-1184.
Douce et al. "Mutants of *Escherichia coli* heat-labile toxin lacking ADP-ribosyltransferase activity act as nontoxic, mucosal adjuvants" Proc. Natl. Acad. Sci, USA, vol. 92, Feb. 1195; pp. 1644-1648.
Van Ginkel et al. "Cutting Edge: The Mucosal Adjuvant Cholera Toxin Redirects Vaccine Proteins into Olfactory Tissues" The Journal of Immunology, pp. 4778-4783; 2000.
Muhlradt et al. "Isolation, Structure Elucidation, and Synthesis of a Macrophage Stimulatory Lipopeptide from Mycoplasma fermentans Acting at Picomolar Concentration" The Rockefeller University Press, vol. 85, No. 11, Jun. 2, 1997; pp. 1951-1958.
Burgos et al. "A new, Asymmetric Synthesis of Lipids and Phospholipids" The American Chemical Society, pp. 4973-4977; 1987.

(Continued)

*Primary Examiner* — Robert A Zeman
(74) *Attorney, Agent, or Firm* — W&C IP

(57) ABSTRACT

Disclosed is the use of lipopeptides and lipoproteins as mucosal adjuvants for various vaccinations via mucous membranes, particularly intranasally. Said lipopeptides represent peptides or proteins substituted with 2,3-diacyloxy (2R)-propyl at the amino-terminal cystein of a peptide or protein, preferably S-(2,3-bis-palmitoyloxy-(2R)-propyl) cysteinyl peptides derived from mycoplasmas. Said peptides are highly effective even in small doses, produce good immunization results, and increase the IgA level, among others.

Figure 1:
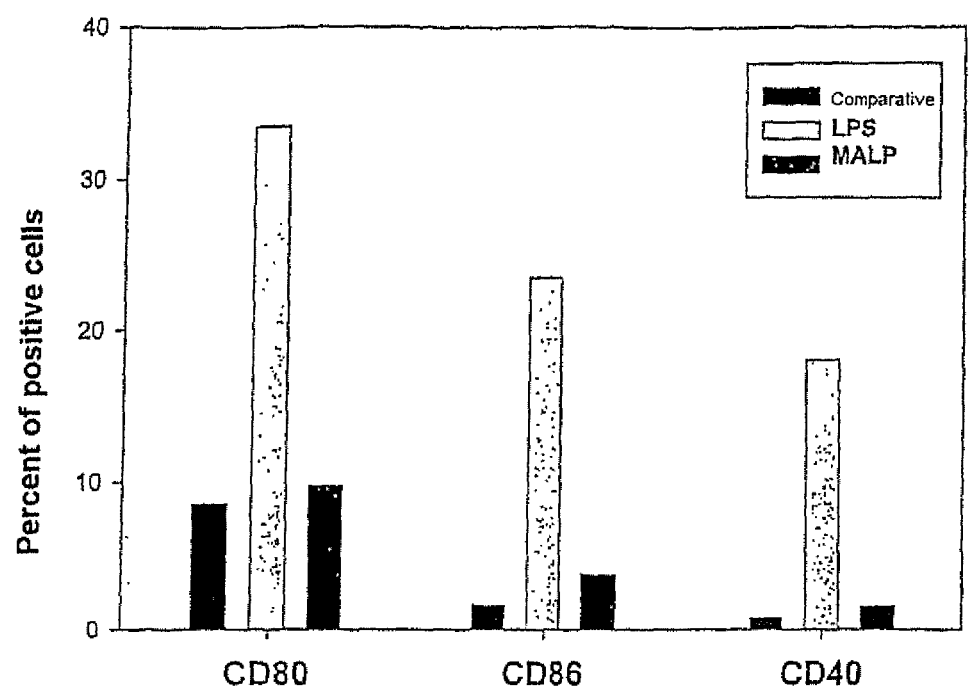

11 Claims, 12 Drawing Sheets
Specification includes a Sequence Listing.

(56) References Cited

OTHER PUBLICATIONS

Morr et al. "Differential recognition of structural details of bacterial lipopeptides by toll-like receptors" Eur. J. Immunol, pp. 3337-3347; 2002.

Holmgren, Jan, et al., "Mucosal adjuvants and anti-infection and anti-immunopathology vaccines based on cholera toxin, cholera toxin B subunit and CpG DNA", Immunology Letters 97 (2005), pp. 181-188.

Yamamoto, M., et al., "Genetically Manipulated Bacterial Toxin as a New Generation Mucosal Adjuvant", Scand. J. Immunol. 53, (2001), pp. 211-217.

* cited by examiner

Expression of specific markers by murine DCs obtained from bone marrow after stimulation with MALP-2 or LPS β-Galactoside-specific serum IgG response stimulated through use of MALP-2 as adjuvant β-Galactosidase-specific serum IgG response stimulated through use of 1 μg of MALP-2 as adjuvant β-Galactosidase-specific proliferative responses stimulated through use of MALP-2 as adjuvant Determination of serum IgE in animals immunized with use of MALP-2 as adjuvant

SEQUENCE LISTING

<160> NUMBER OF SEQ ID NOS: 4

<210> SEQ ID NO 1
<211> LENGTH: 5
<212> TYPE: PRT
<213> ORGANISM: Mycoplasma fermentans

<400> SEQUENCE: 1

Gly Gln Thr Asn Thr
1               5

<210> SEQ ID NO 2
<211> LENGTH: 5
<212> TYPE: PRT
<213> ORGANISM: Mycoplasma fermentans

```
<400> SEQUENCE: 2

Ser Lys Lys Lys Lys
1               5

<210> SEQ ID NO 3
<211> LENGTH: 13
<212> TYPE: PRT
<213> ORGANISM: Mycoplasma fermentans

<400> SEQUENCE: 3

Gly Asn Asn Asp Glu Ser Asn Ile Ser Phe Lys Glu Lys
1               5                   10

<210> SEQ ID NO 4
<211> LENGTH: 20
<212> TYPE: PRT
<213> ORGANISM: Mycoplasma fermentans

<400> SEQUENCE: 4

Gly Gln Thr Asp Asn Asn Ser Ser Gln Ser Ala Ala Pro Gly Ser Gly
1               5                   10                  15

Thr Thr Asn Thr
            20
```

USE OF A LIPOPEPTIDE OR LIPOPROTEIN AS AN ADJUVANT IN THERAPEUTIC OR PROPHYLACTIC VACCINATIONS

CROSS REFERENCE TO RELATED APPLICATIONS

This application is a Continuation Application of U.S. application Ser. No. 10/509,917 filed Apr. 10, 2004 which is a National Stage Application based on the International Application No. PCT/DE2003/003497 filed Apr. 3, 2003 which claims priority to German Application 02007640.2 filed Apr. 4, 2002.

The invention relates to the use of a lipopeptide or lipoprotein as adjuvant in therapeutic or prophylactic vaccination, especially via the mucous membranes, i.e. as mucosal adjuvant.

A third of all deaths each year in the world are even now caused by infectious diseases, which are additionally responsible for at least 15% of new cancers. Infectious diseases are thought also to be involved in the pathophysiology of various chronic inflammatory, vascular or degenerative diseases. Infectious diseases are the cause of high costs to the general public through treatment costs and patients' absence from work.

To combat infectious diseases, in general two routes are followed, namely therapy and prophylaxis. In this connection, immunizations have become the most effective weapon against infectious diseases. However, there are still many infectious diseases for which no vaccine is yet available or adequate immunization cannot be achieved. Many vaccines are inadequate because of low efficiency, serious side effects, low stability or high costs. There is thus a great need for novel and improved immunizing substances (vaccines).

Vaccines have traditionally been used for prophylaxis of infectious diseases and are satisfactory in this area for many diseases. Recent findings suggest that vaccinations additionally are a very suitable means for the immunotherapy of other transmissible diseases for which immunization has not yet been done, such as viral hepatitis, *Helicobacter pylori* infections, herpes virus infections etc. A further area of use is the incorporation of vaccines in immunotherapies and immunoprophylaxes for autoimmune diseases, inflammatory diseases, tumors, allergies and for contraception in humans and animals. In some cases (especially including the last case mentioned), the usability of vaccines appears to be linked to an efficient mucosal administration route and the generation, associated therewith, of a good mucosal immune response.

Most infections are either confined to the mucous membranes, or the pathogens must pass through the mucous membrane in early phases of the infection. The absolute aim with a vaccination must therefore be to obtain not only a systemic but in particular also a mucosal immune response in order thereby primarily to stop both the infection (colonization) and the development of the disease. A good mucosal immune response would distinctly reduce the risk of transmission.

The fact that the systemic and the mucosal immune system partly overlap but are not identical means that parenterally administered vaccines are less effective for protection against mucosal pathogens (McGhee, Mestecky et al., "The mucosal immune system: from fundamental concepts to vaccine development", Vaccine 10, 75-88 (1992)). In fact, parenterally administered vaccines essentially stimulate systemic immune responses, whereas vaccines administered by a mucosal route, i.e. via the mucous membranes, simulate the immune response elicited by natural infections. In this way, mucosal immunization leads to effective systemic and mucosal immune responses.

It is further to be expected that mucosal administration of vaccines will be associated with fewer side effects and be readily accepted by patients. Vaccines are easier to administer by a mucosal route and can be brought better into compliance with vaccination protocols. Provision thereof is associated with lower costs.

The administration of antigens by a mucosal route has to date been associated with some considerable difficulties. A major problem is that the antigens administered in this way are frequently scarcely immunogenic. This derives from various mechanisms such as (i) increased rate of antigen elimination by non-specific clearance mechanisms of the host (for example siliary activity, peristalsis), (ii) antigen degradation by locally acting enzymes, (iii) antigen alteration and/or structural modification as a result of extreme pH values (acidic medium in the stomach, alkaline in the intestinal tract), (iv) low antigen permeability of the mucous membranes and (v) only very limited access to antigen-presenting cells.

Various strategies have been used to overcome these difficulties, e.g. inclusion or association of the antigens with particles (microparticles, nanoparticles, bacteria or bacterial fragments) as carriers, use of virus-like constructs; use of liposomes or ISCOMS (immunostimulatory complexes) or virosomes, use of transgenic plants, antigen production by attenuated viral or bacterial carriers, either as conventional vectors or as carriers of nucleic acid vaccines and/or administration of these aids with mucosal adjuvants. Despite intensive efforts in this area, to date virtually no sufficiently effective and at the same time well-tolerated mucosal adjuvants have achieved practical use.

Substances referred to as "adjuvants" are those which are added in an immunization to the actual antigen (i.e. the substance which provokes the desired immune response) in order to enhance the humoral and/or cell-mediated immune response ("Lexikon der Biochemie und Molekularbiologie", 1. Band, Spektrum, Akademischer Verlag$^{1995}$). The use of many adjuvants is based solely on experience, and the effect can neither be accurately explained nor predicted. The following groups of adjuvants are traditionally used in particular: aluminum hydroxide, emulsions of mineral oils, saponins, detergents, silicon compounds, thiourea, endotoxins of gram-negative bacteria, exotoxins of gram-positive bacteria, killed bacteria or parts thereof.

The use of optimal adjuvants plays a crucial role in vaccination. Antigens administered without adjuvant only rarely mediate an adequate immune response. In addition, not only the strength but also the quality of the elicited immune response matters. Stimulation of an incorrect immunization pattern may lead to immunopathological reactions and exacerbation of the symptoms of infection. In this context, the adjuvant can help to assist the desired immune response.

Adjuvants approved for humans are limited. One of the few adjuvants accepted by approval authorities for humans is aluminum hydroxide. It is not possible to conclude from the fact that an adjuvant is active on systemic administration, i.e. assists the effect of an antigen, that this also applies to other administration routes. A typical example is aluminum hydroxide which can assist the immunogenicity of a substance on intramuscular, subcutaneous, intraperitoneal or intradermal administration but remains completely ineffective on mucosal administration.

There has been an intensive search in recent years for novel adjuvants, including those for the mucosal administration route. Only a few substances have been found to be able to enhance mucosal responses. Among these, some act as carriers to which the antigens must be bound or fused thereto. Far fewer universally employable "true" adjuvants which are admixed to the antigens have been found.

True mucosal adjuvants which have been discovered are the heat-labile toxin from *Escherichia coli* and the cholera toxin from *Vibrio cholerae*. Both have been described as having activity as mucosal adjuvant (Holmgren et al, "Cholera toxin and cholera B subunit as oral-mucosal adjuvant and antigenvector system", Vaccine 1179-1184, 1993 and Douce et al, "Mutants of *Escherichia coli* heat-labile toxin lacking ADP-ribosyltransferase activity act as nontoxic, mucosal adjuvants", Proc. Natl. Acad. Sci. USA 92, 1644-1648). However, their intrinsic toxicity and the potential side effects are detrimental to their usability in connection with human vaccinations. Although non-toxic derivatives of these molecules have been produced by genetic engineering, severe, intolerable side effects are still reported, such as pathological changes in the respiratory mucosa and penetration of the toxin into the brain (N. Gargon, presentation at the "Word Vaccine Congress", Geneva, 26 to 28 Sep. 1999; and: van Ginkel, F. B. et al., "cutting edge: The Mucosal Adjuvant Cholera Toxin Redirects Vaccine Proteins into Olfactory Tissues", J. Immunol. 2000, 165, 4778-4782).

There is thus still a pressing need for novel tolerated and effective mucosal adjuvants.

The invention was therefore based on the object of developing a range of novel, highly active mucosal adjuvants which are non-toxic for humans and which can be employed with a wide variety of active ingredients to be assisted in conventional or novel vaccines such as, in particular, prophylactic or therapeutic vaccines including cancer and DNA vaccines.

This object is achieved by providing the use of a lipopeptide or lipoprotein of the structure (I) as mucosal adjuvant in therapeutic or prophylactic vaccination via the mucous membranes,

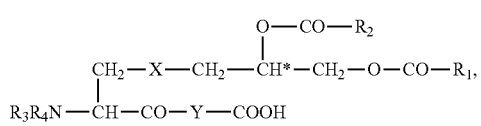
(I)

where
$R_1$ and $R_2$, which may be identical or different, are $C_{7-25}$-alkyl, $C_{7-25}$-alkenyl or $C_{7-25}$-alkynyl,
X is S, O or $CH_2$,
$R_3$ and $R_4$ are independently of one another H or methyl and Y is a physiologically tolerated amino acid sequence which consists of 1 to 25 amino acid residues and is not immunogenic per se in the species used,
and the asymmetric carbon atom marked with * as the absolute R configuration when X is S (sulfur), according to the Cahn-Ingold-Prelog rule.

Although DE 19652586 A1 has already mentioned inter alia the use of a particular S-(2,3-dihydroxypropyl)cysteinpeptide with two fatty acids linked in ester fashion to the dihydroxypropyl group as vaccine adjuvant, this was purely hypothetical and without reference to mucosal adjuvants, so that a conventional vaccination route is to be assumed.

The amino acid sequence (Y) linked carboxy-terminally to the 2,3-diacyloxypropyl-substituted amino acid is preferably selected from the following sequences:

a)
GQTNT, b)
SKKKK, c)
GNNDESNISFKEK
or d)
GQTDNNSSQSAAPGSGTTNT.

Particularly preferred at present is an S-[2,3-bispalmitoyloxy-(2R)-propyl]cysteinyl-peptide where the peptide chain may in turn be a physiologically tolerated amino acid sequence which consists of 1 to 25 amino acids and is not immunogenic per se in the species used.

According to current knowledge, the carboxy-terminal peptide chain might have a function which controls and, where appropriate, modifies the hydrophilicity or lipophilicity of the lipopeptide, so that it is possible in general to use all peptide or protein chains which—depending on the purpose for which the vaccine is employed—satisfy this criterion. The peptide chain should be physiologically tolerated and, in particular, not itself immunogenic in the species used (i.e. the immunized (vaccinated) species, whether human or animal).

At present, the structure according to formula (I) is regarded as crucial for the activity as mucosal adjuvant, with the asymmetric center at the identified point appearing to have a central importance.

The mucosal adjuvant of the invention can be linked by all methods known to the skilled worker to the antigen or active molecule intended for the vaccination, be incorporated together with the latter in physical (e.g. microparticles, nanoparticles, liposomes, ISCOMS, polymers) or biological particles (bacteria, bacterial parts) or virosomes or be mixed with the antigen. For binding to carriers it is also possible to provide transport molecules or transport proteins as carriers.

The lipoprotein or lipopeptide according to the above-mentioned formula (I) which is used according to the invention is preferably present in a preparation with the active vaccination component (e.g. the antigen) which is suitable and provided for intranasal, intra-NALT (nasal associated lymphoid tissue), aerosolized, oral, intrarectal, conjunctival, intravaginal, intraurethral administration or for administration into the milk ducts of the female breast. Alternatively, the mucosal adjuvant of the invention can be present in a kit for coadministration with a vaccine by one of the aforementioned routes and be adapted therefore where appropriate.

The lipopeptide or lipoprotein of the invention is obtained in particular by synthesis. Lipopeptides of the invention might also be obtained by methods generally known in the art from a mycoplasma clone and particularly advantageously from a *Mykoplasma fermentans* clone. The lipopeptides of the invention are also referred to as MALP, namely as "macrophage-activating lipopeptides". These include different variants, of which MALP-2 is a 2 kDa lipopeptide according to formula (I) with Y=GNNDESNISFKEK; $R_3$, $R_4$=H and $R_1$, $R_2$=palmitoyl(C15) (S-(2,3-bispalmitoyloxypropyl)cysteinyl-GNNDESNISFKEK).

Synthesis of the lipopeptides and -proteins of the invention can advantageously be carried out by the method in "Synthesis of $N_\alpha$-Fmoc protected derivates of S-(2,3-dihydroxylpropyl)-cysteine and their application in peptide synthesis", J. W. Metzger, K.-H. Wiesmüller, G. Jung in: Int. J. Peptide Proteine Res. 38, 1991, 545-554". However, the natural (obtained for example from a mycoplasma clone) corresponding lipopeptides are erroneously referred as having the S configuration, although the same compounds ought according to the internationally valid Cahn-Ingold-Prelog nomenclature be referred to as having the R configuration (see, for example, D. Chapman in "Introduction to Lipids", McGraw-Hill, London, 1969, p. 67 zu "Phosphoglycerides"; Burgos et al. J. Org. Chem. 1987, 52 4973-4977; Morr et al. Eur. J. Immunol. 2002, 32:3337-3347).

In a further development of the invention, the lipopeptide or lipoprotein may be present in a preparation with at least one further adjuvant and/or antigen. It is possible in particular for it to be administered together with one or more anti-inflammatory, antiangiogenic, cytotoxic or immunomodulatory substances or ligands (e.g. chemokines, cytokines, CD40 ligand) or with antibodies, or in a preparation therewith.

The lipopeptide or lipoprotein may also, as already mentioned above, be associated or connected to a physical or biological carrier. It may furthermore be present and employed in a preparation with further additives and excipients, in particular preservatives or stabilizers.

The invention represents a great advance in the efforts to provide effective mucosal adjuvants: the lipopeptide can be modified within the framework of formula (I) and thus its qualitative and quantitative activity can be varied and adapted to the desired use. It can be prepared at comparatively reasonable cost and is non toxic for humans. Admixture of comparatively small amounts suffices in most cases for distinct enhancement effects. The lipopeptides of the invention are well characterized in terms of their chemical and biochemical properties and can be obtained sufficiently pure in particular by synthetic routes (Mühlradt, P. F., M. Kiess, H. Meyer, R. Sussmuth, G. Jung (1997), Isolation, structure, elucidation, and synthesis or a macrophage stimulatory lipopeptide from *Muycoplasma fermentans* acting at picomolar concentration"; J. Exp. Med. 185: 1951; and Takeuchi, O., A. Kaufmann, K. Grote, T. Kawai, K. Hoshino, M. Morr, P. F. Mühlradt, and S. Akira (2000); "Cutting edge: Preferentially the R-stereoismoser of the mycoplasmal lipopeptide macrophage-activating lipopeptide-2 activates immune cells through a toll-like receptor 2- and MyD88-dependent signaling pathway"; J. Immunol. 164:554), and thus serious side effects are not according to current knowledge to be expected.

A further advantage of the invention is that on immunizations with admixture of the mucosal adjuvant of the invention there were found to be high concentrations of IgA in the mucosal secretions of treated experimental animals. This antibody species is particularly important for protecting the mucous membranes from infections.

Since at present absolutely no effective adjuvants are approved for intranasal immunization of human patients, the invention represents a significant medical advance in this area.

The lipopeptides or lipoproteins of the general structure (I) described in this invention can also be used generally, i.e. by other routes than mucosal, as adjuvants, including particular administrations for DNA vaccines and cancer vaccines, vaccines against non infectious diseases and the like, excluding the previously known MALP-2 peptides, namely S-(2,3-diacyloxypropyl)cystein-peptides of the sequence DhcGNNDESNISFKEK, where N-terminally the amino acids at positions 2 and, where appropriate, 3 may be absent and/or C-terminally 1 to 2 amino acids may be deleted, for the conventional vaccination routes (intramuscular, subcutaneous, intradermal, intraperitoneal).

The adjuvants of the invention can be combined with a wide variety of antigens to give vaccines. Antigens which can be selected are, in particular, target antigens for the prophylaxis and treatment of infectious diseases, tumors, autoimmune diseases, allergies, and chronic or acute inflammatory diseases. The selection may be made inter alia from the antigen pool of infective agents such as viruses, bacteria, parasites, rickettsia, mycoplasma, fungi and the like. An immunization also means a treatment with antigens for fertility control in human or animal populations.

The advantageous properties of the mucosal adjuvant of the invention which are evident from the examples cannot be inferred from any publication prior to this application.

Methodological Approach to the Experiments/Investigations

At the outset, in vitro screening studies were initially carried out in order to be able to estimate the potential of the investigated lipopeptides in relation to the activation of antigen-presenting cells. The target cells used were dendritic cells derived from the bone marrow, which were obtained from precursors with the aid of GM-CSF. Entirely in contrast to what could be expected on the basis of the activity of MALP-2 in relation to macrophages, MALP-2 showed only weak activity on primary dendritic cells. Compared with the control samples, which had been incubated in the presence of *E. coli* lipopolysaccharides (LPS, 10 ng/ml), only a very weak activation of dendritic cells treated with 5 ng/ml MALP-2 was observed.

On the basis of these preliminary investigations it was not possible to expect MALP-2 and corresponding lipopeptides to be suitable as adjuvant, because a certain ability to activate dendritic cells is presumed for adjuvants. Dendritic cells are the principal group of antigen-presenting cells. They play a central part in the primary immune response, where they (1.) represent the most efficient antigen-presenting cells, (2.) are the most important source of epitopes for specific T-cell clones, and (3.) are the most important activators of resting T cells able to elicit primary immune responses in vivo. Whereas LPS-treated dendritic cells show a strong up regulation or multiplication of CD40 including CD80 and CD86, only a weak effect, or none, is noticeable in dendritic cells treated with MALP-2.

This was to some extent to be expected and consistent with the results obtained on macrophages. It had been found with them that, after an initial up regulation phase, as treatment with MALP-2 continued there was an increased turnover and reduced expression of MHC class II molecules which are essential for correct antigen presentation (M. Frisch et al., Eur. J. Immunol. (1996) 26, 1050-1057). The effect found for the adjuvant is all the more surprising.

The results of the preliminary experiments were therefore initially strongly against a possible activity of the lipopeptides and -proteins investigated here as adjuvants.

Although it was obvious from these in vitro studies that the lipopeptides in question promised no success in this regard, they were included as negative control samples, namely as examples of macrophage-activating substances of low activity, in in vivo studies by the inventors, because the substances were available from earlier experiments.

Surprisingly, because in complete contrast to the in vitro experiments, it was found that, for example, MALP-2 was able on administration together with the model antigen β-galactosidase by either the intranasal (i.n.) or intraperitoneal (i.p. (note: in the animal model)) route in a dose of only 0.5 µg per animal per dose, to increase the β-galactosidase-specific IgG serum titers by 675 to 3560 fold (i.n.) and 64 to 128 fold (i.p.). It is possible on use of the lipopeptides of the invention to elicit almost maximum IgG responses even after the first immunization, and these IgG titers correspond to those on administration of 10 µg (three-molar excess) of cholera toxin subunit B (CTB), a well-characterized mucosal adjuvant. Similar results are found on intradermal or subcutaneous administration of the lipopeptides and -proteins of the invention. It is therefore to be assumed that administration of the lipopeptides and -proteins of the invention can and ought to take place in a (molar) concentration which is at least 3 times lower than with conventional adjuvants.

It was also possible to show that administration of the lipopeptides of the invention by the intranasal route leads to an effective stimulation of the mucosal immune system overall. Thus, on administration of MALP-2 as adjuvant to the model antigen, respectively 36% and 23% antigen-specific IgA, based on the total IgA, were found in lung and vaginal lavages. This shows that the lipopeptides of the invention are not only able to elicit local mucosal immune responses, but the spread of Iga-producing cells to other remote areas of mucous membranes takes place to an extent leading to good mucosal immune responses. This effect is linked to the mucosal administration route.

Administration of the lipopeptides of the invention with the antigen also elicited stronger cellular immune responses than did CTB, both regionally in lymph nodes and in the spleen (p<0.05). Analysis of β-galactosidase-specific IgG isotypes and the profiles of the cytokines secreted by cells stimulated in vitro showed that administration with the lipopeptides induced a dominant Th2 response pattern. The results of the investigations therefore prove that the lipopeptides of the invention represent effective adjuvants for mucosal administration of antigens in vaccines.

An important aspect which should be assessed here is that an incremental rise in the lipopeptide dose (starting from the optimal doses mentioned herein) leads to a steady reduction in the immune response. This contrary effect is unexpected and could not have been inferred from the prior art.

EXAMPLE SECTION

General

The investigations described in the examples were mainly carried out with a synthetic MALP-2, which substantially corresponds to a lipopeptide derived from mycoplasma, as mucosal adjuvant together with β-galactosidase as model antigen. This specific exemplary lipopeptide was selected on the basis of its previously determined intrinsic properties (biochemical properties, macrophage-stimulating activity). Unless indicated otherwise, the synthetic lipopeptide S-[2,3-bispalmitoyloxypropyl]cysteinyl-GNNDESNISFKEK which was used in the examples is always referred to simply as "MALP-2" hereinafter.

The MALP-2 doses were initially established in preliminary studies in which MALP-2 was administered subcutaneously, intradermally, intranasally or intraperitoneally to mice. In all protocols, simultaneous or associated administration of MALP-2 with β-galactosidase led to a significant increase in the production of β-galactosidase-specific antibodies.

The induced immune responses obtained in the presence of MALP-2 after immunization by the intranasal or intraperitoneal route were then analyzed and compared with those obtained in comparative experiments with CTB as adjuvant.

The examples reveal that use of MALP-2 in a dose of only 0.5 µg per administration led to a significant increase both in the humoral and in the cellular β-galactosidase-specific responses. Even intraperitoneal administration led to an improved immune response, but the intranasal route proved to be far more effective. By comparison therewith, a three-fold molar excess of CTB was necessary to obtain comparable systemic or mucosal humoral responses. Concerning the cellular responses, spleen cells from mice immunized with MALP-2 showed distinctly higher proliferation ($p<0.05$) than those from animals vaccinated with the three-fold molar excess of CTB.

The primary response obtained with MALP-2 as adjuvant by the intranasal route was characterized in terms of the kinetics of the β-galactosidase-specific antibody response through the presence of high antibody titers, which almost reached the maximum plateau even after the first immunization. Humoral and cellular responses were stronger after i.n. vaccination, indicating a differential local effect of MALP-2, which might be attributed either to its bioavailability or the spatial distribution of the specific receptors in the target cells. As already described, distinct immune responses were found even in mucosal tissues not directly reachable by the vaccination route, namely β-galactosidase-specific IgA in lung and vaginal lavages.

The investigations within the scope of the invention have therefore revealed that the lipopeptides of the invention are novel and potent mucosal adjuvants, it being unnecessary, in contrast to other lipopeptides, to conjugate the target antigen with the active lipopeptide.

Throughout the experiments with the immunized animals, no serious side effects or signs of acute or chronic toxicity were observed. The relatively short peptide unit within the lipopeptides of the invention means that the immunogenicity is relatively low, thus minimizing the risk of immune responses against the lipopeptides themselves. This represents a distinct advantage over proteins as adjuvants. No anti-MALP-2 antibodies were detectable after intranasal administration of MALP-2 as adjuvant. This represents a distinct advantage over proteins as adjuvants, because an immune response against the adjuvant itself may impair a later immune response against another vaccine administered with the same adjuvant. The lipopeptides of the invention can be employed in vaccines against a wide variety of pathogens and in cancer vaccines or vaccines for fertility control. Further advantages of the invention are the good stability of the lipopeptides during storage, greater purity of the lipopeptides which can be prepared by synthesis, and predictable chemical and biochemical behavior.

KEY TO THE FIGURES

FIG. 1. In vitro investigations with primary dendritic cells:

Primary dendritic cells from the bone marrow of BALB/c mice were obtained by in vitro maturation of precursors using recombinant GM-CSF ($5\times10^4$ U/ml). The mature dendritic cells were stimulated with 10 ng/ml E. coli lipopolysaccharide (LPS) or 5 ng/ml MALP2. The cells were then doubly labeled with CD11c-specific antibodies (dendritic cell markers) in combination with anti-CD40 or anti-CD80 or anti-CD86. Expression of CD40 or CD80 or CD86 in the CD11c-labeled cells was analyzed with the aid of flow cytometry. The results are expressed as a percentage of positive cells relative to the total CD11c-positive population.

Figure 2:
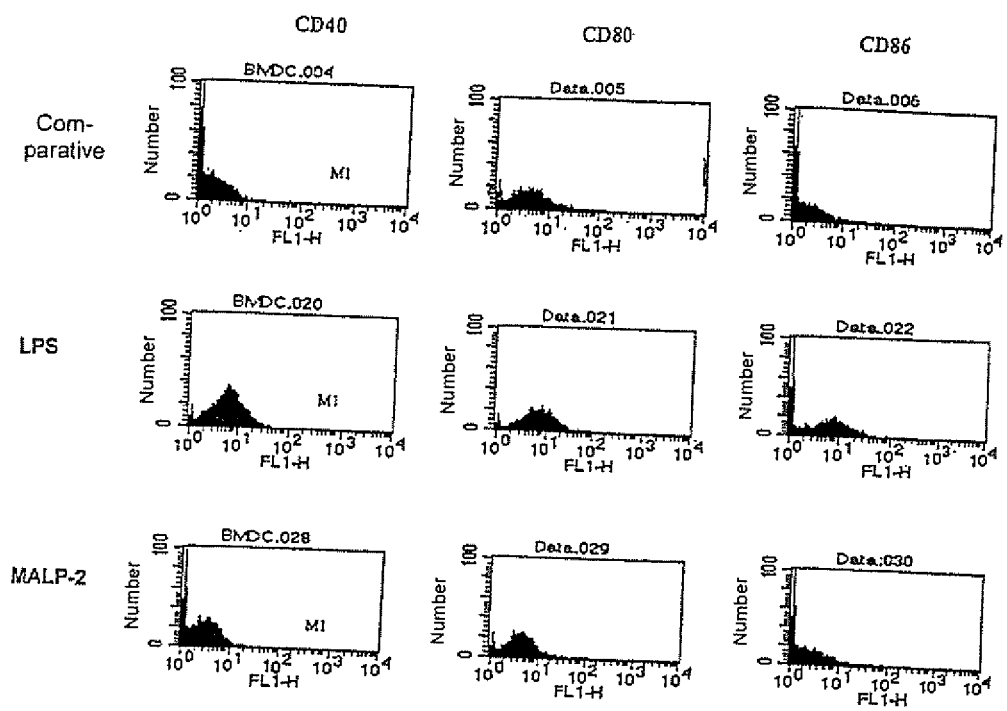

FIG. 2. Analysis of dendritic cells after treatment with MAPL-2 with the aid of flow cytometry (FACScan):

Primary dendritic cells from the bone marrow of BALB/c mice were obtained by in vitro maturation of precursors using recombinant GM-CSF ($5 \times 10^4$ U/ml). The mature dendritic cells were stimulated with 10 ng/ml E. coli lipopolysaccharide (LPS) or 5 ng/ml MALP2. The cells were then doubly labeled with CD11c-specific antibodies (dendritic cell markers) in combination with anti-CD40 or anti-CD80 or anti-CD86 and the cells were analyzed with the aid of flow cytometry. The gates were set on the basis of a labeling with unrelated control antibody isotopes.

Figure 3:
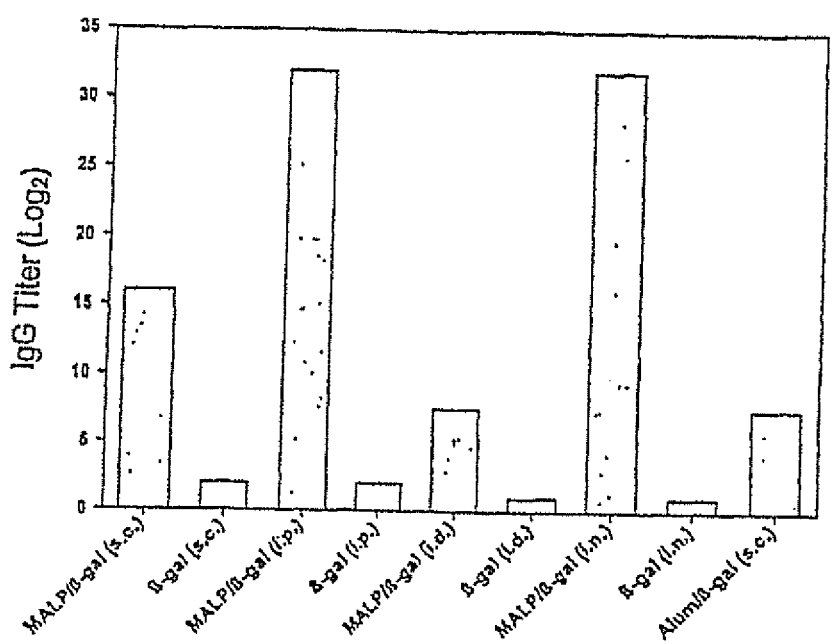

FIG. 3. Humoral responses stimulated after immunization with MAPL-2 as adjuvant:

Mice were immunized by subcutaneous (s.c.), intraperitoneal (i.p.), intradermal (i.d.) and intranasal (i.n.) routes with either pure β-galactosidase (40 μg) or β-galactosidase mixed with MALP-2 (0.5 μg) on days 0, 7 and 14. On day 28 after the primary immunization, serum samples were removed and the titer of β-galactosidase-specific antibodies was determined by means of an ELISA. The results are shown as reciprocal $\log_2$ of the geometric mean of the endpoint titer. As a control, we included a group in which the animals were immunized by the route with β-galactosidase using aluminum hydroxide as adjuvant.

Figure 4:
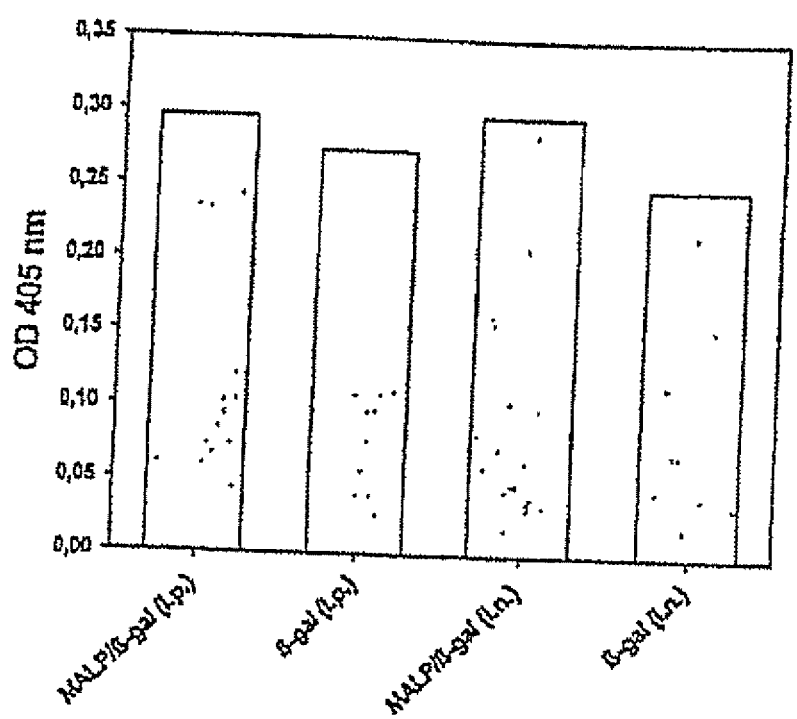

FIG. 4. Humoral responses stimulated after immunization using MALP-2 as adjuvant in a dose of 1 μg per animal and immunization:

Mice were immunized by the intraperitoneal (i.p.) and intranasal (i.n.) route with either pure β-galactosidase (40 μg/dose) or β-galactosidase mixed with MALP-2 (1 μg/dose) on days 0, 7 and 14. On day 28 after the primary immunization, serum samples were taken and the titer of β-galactosidase-specific antibodies was determined by means of an ELISA. The results are shown as absorbances (OD 405 mm).

Figure 5:
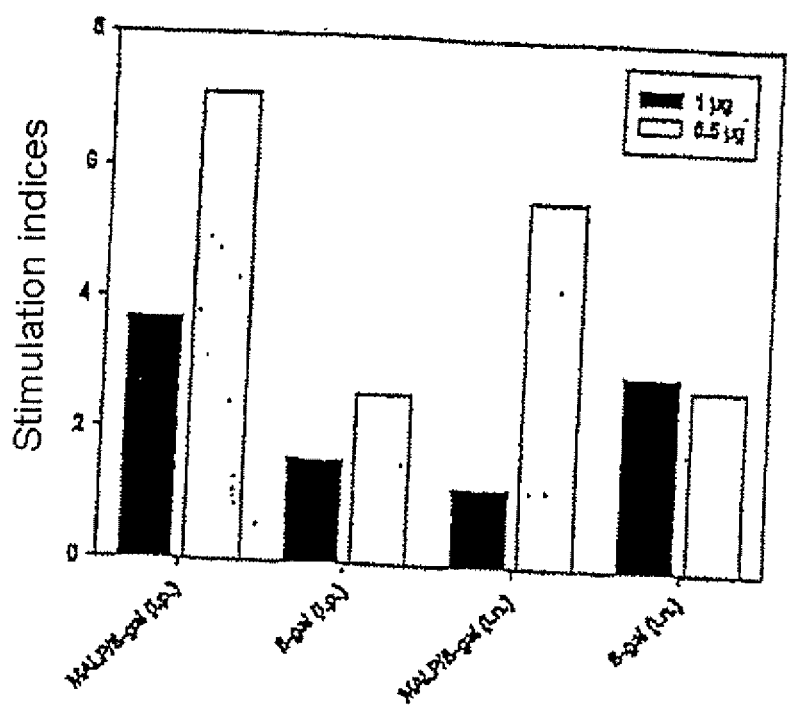

FIG. 5. Cellular responses stimulated after immunization using different concentrations of MALP-2 as adjuvant.

β-Galactosidase-specific T-cell proliferation responses of mouse spleen cells immunized by the i.p. or i.n. routes with either pure β-galactosidase (40 μg/dose) or β-galactosidase mixed with MAPL-2 (1 or 0.5 μg/dose) on days 0, 7 and 14. On day 28 after the primary immunization, the animals were sacrificed and the spleen cells were restimulated in vitro in the presence of 20 μg/ml soluble β-galactosidase for four days. The results are shown as stimulation indices (cpm of samples/cpm in unstimulated control cells).

Figure 6:
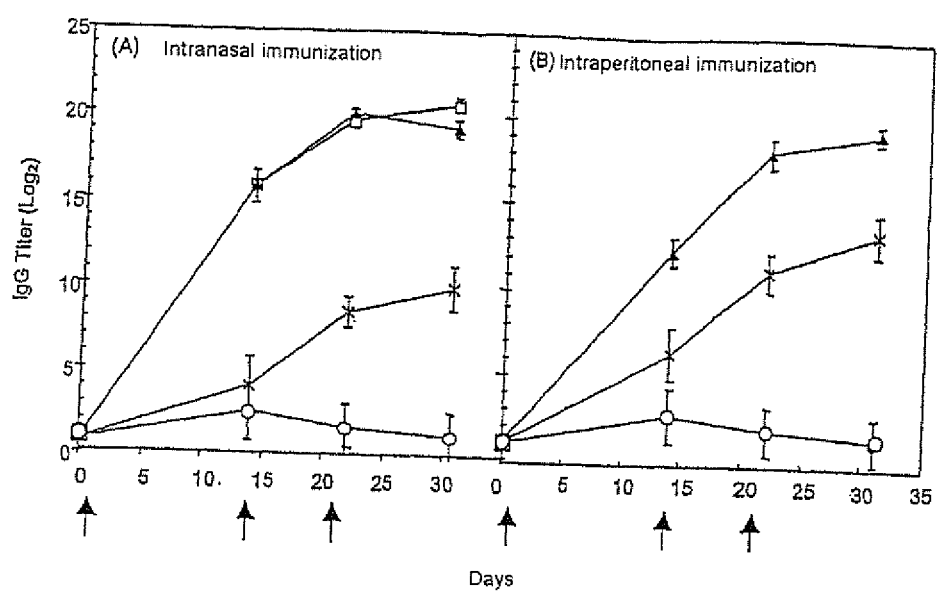

FIG. 6. Kinetics of β-gal-specific IgG responses in sera of immunized mice:

Groups of animals (n=5) were immunized either i.n. (A) or i.p. (B) with 50 μg of β-gal ( ), β-gal plus 10 μg of CTB ( ), β-gal plus 0.5 μg of MALP-2 ( ) or pure buffer solution ( ). The days of the immunizations (day 0, 14 and 21) are marked by arrows. The results are shown as the reciprocal $\log_2$ of the geometric endpoint titer, and the SEM (average standard deviation) is indicated by means of vertical lines.

Figure 7:
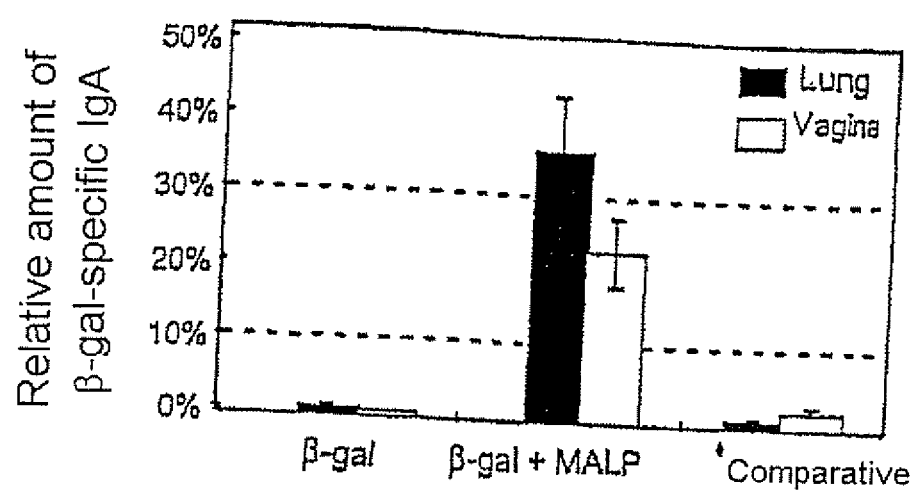

FIG. 7. β-Galactosidase-specific IgA in lung and vaginal lavages from mice immunized i.n.:

The results are shown as percentage of β-galactosidase-specific IgA in relation to the total IgA present. The SEM is indicated by vertical lines.

Figure 8:
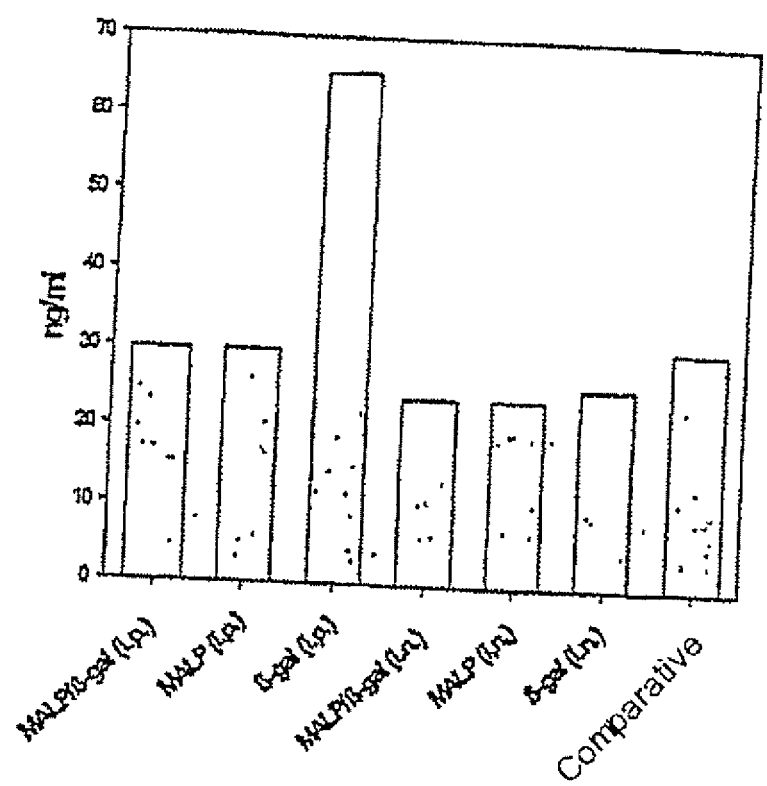

FIG. 8. Determination of the serum IgE level after immunization using MALP-2 as adjuvant:

Mice were immunized intraperitoneally (i.p.) and intranasally (i.n.) either with pure β-galactosidase (40 μg), exclusively MALP-2 or β-galactosidase mixed with MALP-2 (0.5 μg) on days 0, 7 and 14. On day 28 after the first immunization, serum samples were obtained, and the IgE levels were determined by means of a capture ELISA. The results are shown as IgE concentrations (ng/ml).

Figure 9:
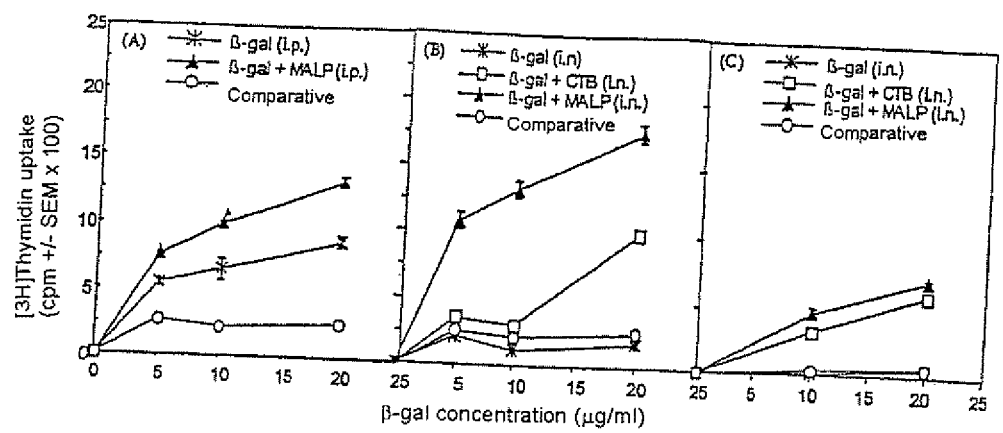

FIG. 9. β-Galactosidase-specific T-cell proliferation responses of the spleen (A and B) and regional lymph node cells (C) of mice immunized i.p. or i.n.:

The cells were restimulated in vitro with various concentrations of soluble β-galactosidase for four days. The results are shown as average cpm subtracted from the background values for unstimulated cells from groups of three. The SEM is depicted by vertical lines.

Figure 10:
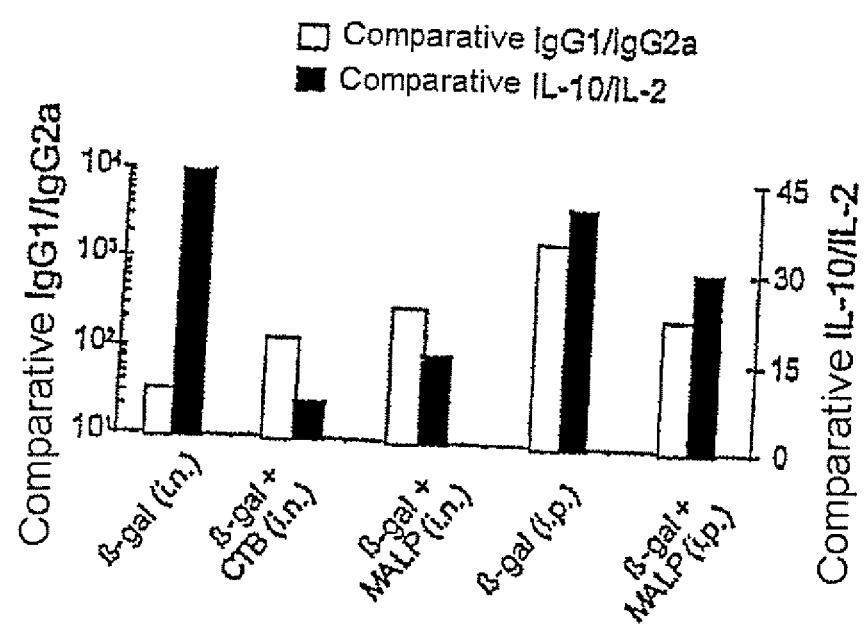

FIG. 10. The profiles stimulated in immunized mice: Serum-β-galactosidase-specific IgG isotypes and cytokines secreted by spleen cells stimulated in vitro were determined for the immunized mice by means of an ELISA. The results are shown as ratios of IgG1/IgG2a and IL-10/IL-2 (the most commonly found cytokines) concentrations.

Figure 11:
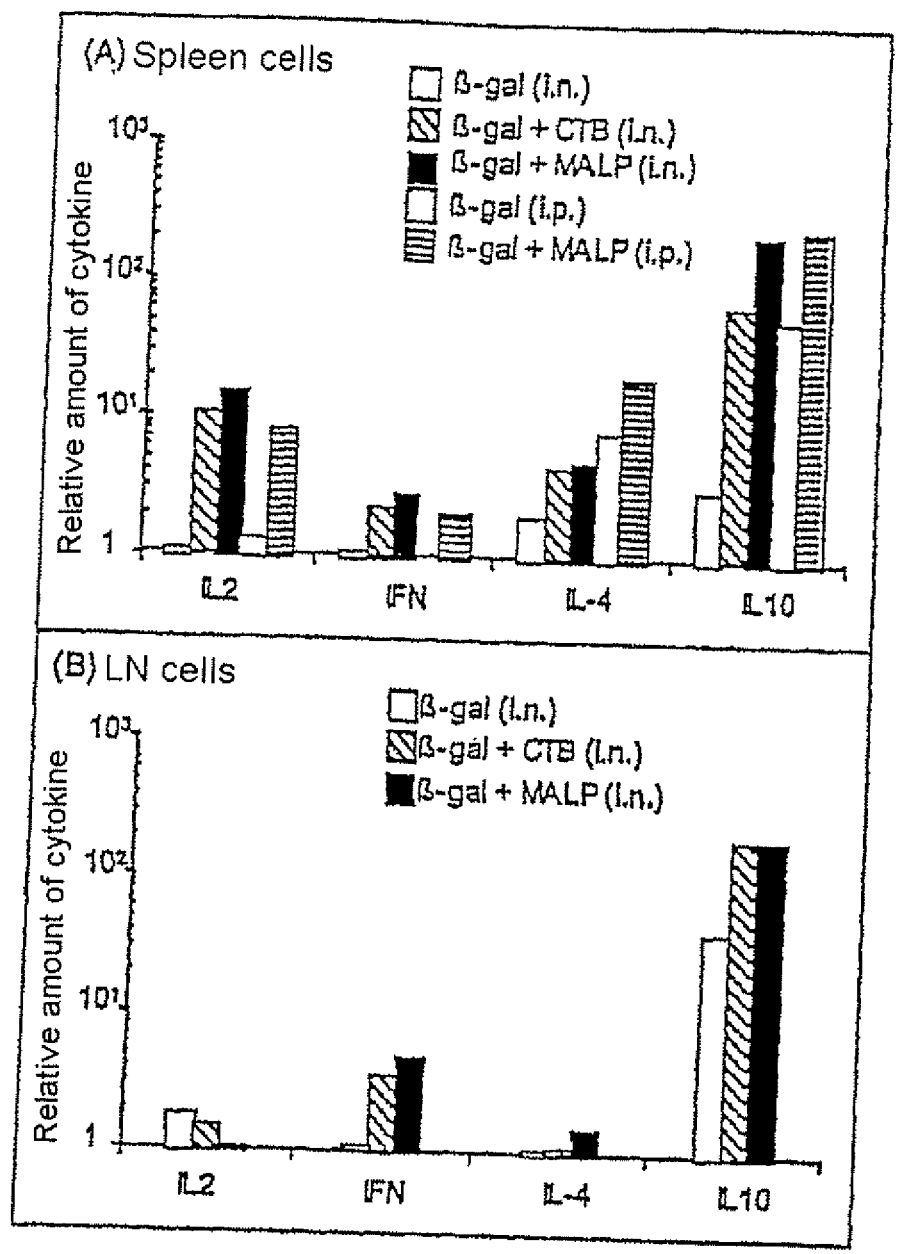

FIG. 11. Cytokines secreted by cells stimulated in vitro from immunized mice:

The cytokine production was measured by means of an ELISA in the liquid supernatant from cells which were cultured in the presence of β-gal (20 μg/ml) for 48 (IL-2) or 96 hours (IFNγ, IL-4 and IL-10). The results are shown as the ratio between the amounts of cytokines found in the immunized groups compared with the unimmunized control mice.

Figure 12:
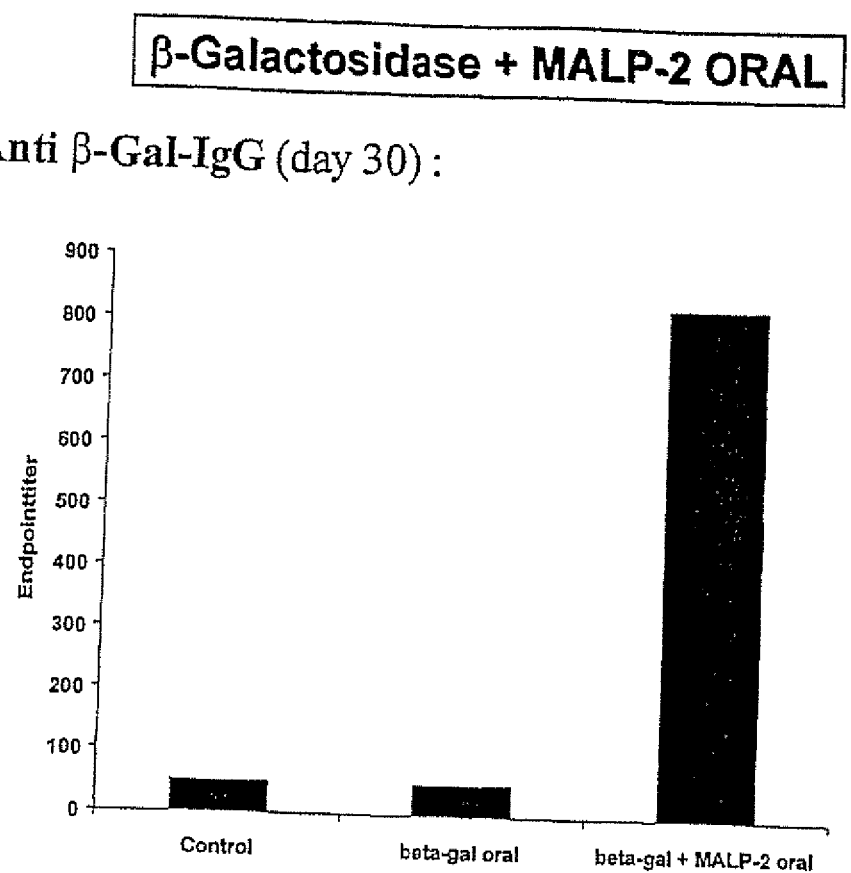

FIG. 12: Humoral responses stimulated after vaccination with MALP-2 as adjuvant in a dose 2 μg per animal per immunization. The mice were immunized orally either with β-galactosidase alone (100 μg/dose) or with β-galactosidase mixed with MALP-2 (2 μg/dose) on days 0, 7, 14 and 31. On day 45 after the first immunization, serum samples were obtained, and the titers of the β-galactosidase-specific antibodies were determined with an ELISA.

EXAMPLE 1: IN VITRO STIMULATION BY MALP-2 OF PRIMARY DENDRITIC CELLS OBTAINED FROM THE BONE MARROW OF RODENTS

Experimental Protocol:

Cultures of primary dendritic cells obtained from the bone marrow were obtained from BALB/c mice after in vitro maturation of precursors in the presence of recombinant GM-CSF ($5 \times 10^4$ U/ml) by the usual methods. The mature dendritic cells were stimulated with E. coli lipopolysaccharide (LPS) or 5 ng/ml MALP2. After stimulation for respectively 12 and 24 hours, the cells were analyzed with the aid of flow cytometry in order to establish the expression of surface markers important for the antibody presentation ability.

In order to define compounds which have a potential as adjuvant for in vivo applications in the area of vaccinations, a first in vitro investigation was carried out with primary cultures of dendritic cells derived from bone marrow. Dendritic cells were selected because they are the most efficient antigen-presenting cells and play a key part in the primary immune response. In fact, they are the only cell type which is able in vivo to activate resting T cells to initiate a primary immune response. Accordingly, dendritic cells were treated with the investigated units or LPS, which served as control. Samples were taken at various times, labeled with fluorescence-labeled antibodies which are specific for cellular markers which are decisive for the antigen-presenting properties of the dendritic cells, and analyzed by flow cytometry.

The results found (FIGS. 1 and 2) show that, differing from the positive control group, the expression of CD40 and the costimulating molecule CD86 in dendritic cells treated with MALP-2 was not increased. The effect on expression of the costimulating molecule CD80 was slight, if present at all. Costimulating molecules emit signals which in addition to the presentation of the epitopes involved within the context of the MHC molecules are essential for effective activation of T cells. It has been reported previously that the effect of proven mucous membrane adjuvants (mucosal adjuvants) such as, for example, cholera toxin is associated with a selective enhancement of the expression of costimulating molecules. Accordingly, the results found in vitro strongly indicate that MAPL-2 has little or no potential as mucosal adjuvant.

EXAMPLE 2: HUMORAL RESPONSES STIMULATED AFTER IMMUNIZATION BY VARIOUS ROUTES USING MALP-2 IN VARIOUS CONCENTRATIONS AS ADJUVANT

Experimental Protocol:

Six- to eight-week old female BALB/c (H-2d) mice were purchased from Harlan Winkelmann GmbH (Borchen, Germany) and treated in accordance with local and EU directives. Groups each of 5 mice were immunized on day 1, 7 and 14 either with 40 µg of pure β-galactosidase (Boehringer, Mannheim, Germany), or with admixture of 1 or 0.5 µg of synthetic MALP-2. For the intranasal administration (i.n.), 10 µl was administered into each nostril, whereas for i.p., s.c. and i.d. injection β-galactosidase was resuspended with or without MALP-2 in respectively 400, 100 and 100 µl of PBS. 28 days after the first immunization, serum samples were taken and stored at −20° C. until the β-gal-specific antibodies were determined. Nunc-Immuno Max-iSorp assay plates with 96 wells (Nunc, Roskilde, Denmark) were coated with 100 µl of β-galactosidase (Boehringer, Mannheim, Germany) with 5 µg/ml in 0.05 M carbonate buffer (pH 8.2) per well. Serum dilutions with 1% BSA and 0.05% Tween-20 in PBS were added (100 µg/well), and the plates were incubated at 37° C. for 24 hours. After rinsing, biotinylated γ-chain specific goat anti-mouse IgG (Sigma Chemie, Deisenhofen, Germany) was added, and the plates were incubated at 37° C. for a further hour. After rinsing four times, 100 µl of peroxidase-conjugated streptavidin (Pharmingen) were added to the cells, and the plates were incubated at 37° C. for 30 minutes. After rinsing four times, the reactions were developed by means of ABTS in 0.1 M citrate-phosphate buffer (pH 4.35) which contained 0.01% $H_2O_2$. The results have been shown either according to the absorption at 405 nm or the endpoint titers (reciprocal $log_2$ of the last dilution which, after incubation for 30 minutes, resulted in an optical density at 405 nm of 0.1 units above the values for the negative control group).

Despite the disappointing results found in the in vitro investigation of primary dendritic cells using MALP-2, we decided to include in the secondary in vivo investigation groups of animals immunized with use of MALP-2 as adjuvant. Accordingly, the mice were immunized i.p., s.c., i.d. and i.n. either with the pure model antigen β-galactosidase or with the antigen plus MALP-2. In contrast to expectations, a strong adjuvant effect was found when the antigen was mixed with 0.5 µg of MALP-2, independently of the mode of administration (FIG. 3). The strongest reactions were found with the i.p. and i.n. immunizations. The responses obtained were, however, always at least as strong as (i.d.) or stronger than on use of aluminum hydroxide as standard adjuvant for s.c. injection (FIG. 3).

Since in preceding investigations using conventional lipopeptides considerably higher concentrations of the component used as adjuvant were given, the effect of higher doses of MALP-2 was to be investigated. For this purpose, animals were immunized with β-galactosidase by the two most effective immunization routes (i.p. and i.n.) with 1 µg of MALP-2 as adjuvant. In contrast to expectations, increasing the dose of MALP-2 led to an abolition of the adjuvant effect (FIG. 4). This showed that we would not have been able to find an adjuvant effect at the level of the humoral responses in the in vivo investigations of MALP-2 on use of the standard concentrations indicated in the literature for other lipopeptides.

EXAMPLE 3: HUMORAL RESPONSES STIMULATED AFTER IMMUNIZATION BY VARIOUS ROUTES USING MALP-2 IN VARIOUS CONCENTRATIONS AS ADJUVANT

Experimental Protocol:

Six- to eight-week old female BALB/c (H-2d) mice were purchased from Harlan Winkelmann GmbH (Borchen, Germany) and treated in accordance with local and EU directives. Groups each of 5 mice were immunized on day 1, 7 and 14 either with 40 µg of pure β-galactosidase (Boehringer, Mannheim, Germany), or with admixture of 1 or 0.5 µg of synthetic MALP-2. For the intranasal administration (i.n.), 10 µl was administered into each nostril, while for the i.p. injection β-galactosidase was resuspended with or without MALP-2 in 400 µl of PBS. The spleens were removed and put together (pooled) for determination of the cellular immune responses. The cells were cultured in RPMI 1640 supplemented with 10% fetal calf serum, 100 U/ml penicillin, 50 µg/ml streptomycin, $5 \times 10^{-5}$ M 2-mercaptoethanol and 1 mM L-glutamine (GIBCO BRL, Karlsruhe, Germany) at 37° C. in a moist atmosphere with 5% $CO_2$. The spleen cell suspensions were adjusted to $5 \times 10^6$ cells/ml in complete medium. They were introduced at 100 µl/well into a flat-bottomed 96-well microtiter plate (Nunc), and these plates were incubated with the addition of 20 µg/ml soluble β-galactosidase for 4 days. During the last 18 hours of culturing, 1 µCi of [$^3$H]thymidine (Amersham International, Freiburg, Germany) were added to each well. The cells were then harvested on filter paper (Filtermat A; Wallac, Freiburg, Germany) with a cell harvester (Inotech, Wohlen, Switzerland), and the amount of [H]thymidine incorporated into the DNA of the proliferated cells was determined with the aid of a γ scintillation counter (Wallac 1450, Micro-Trilux). The results are shown as the arithmetic mean of the [$^3$H]thymidine uptake in cpm. The results are shown as stimulation indices (SI, cpm samples/cpm in unstimulated control cells).

Taking account of the surprising reduction in the adjuvant effect at the humoral level observed on use of MALP-2 in higher dosages, it was decided to find whether a similar effect can be observed at the level of the cellular immune responses. Accordingly, mice were immunized with either pure β-galactosidase or β-galactosidase mixed with 1 µg of MALP-2. Twenty-eight days after the immunization, the spleens were purified, restimulated in vitro with 20 g/ml β-galactosidase, and their ability to proliferate was determined by measuring the incorporation of [$^{3H}$]thymidine in their DNA by means of a γ scintillation counter. The results obtained (FIG. 5) confirmed that the use of MALP-2 in higher dosages not only leads to humoral responses no longer being detectable, but also the cell-mediated immunization is reduced.

EXAMPLE 4: JOINT INTRANASAL AND INTRAPERITONEAL ADMINISTRATION OF MALP-2 WITH A SOLUBLE ANTIGEN STIMULATES EFFECTIVE SYSTEMIC HUMORAL RESPONSES

Experimental Protocol:

Six- to eight-week old female BALB/c (H-2d) mice were purchased from Harlan Winkelmann GmbH (Borchen, Germany) and treated in accordance with local and EU directives. Groups each of 5 mice were immunized on day 1, 14 and 21 either with 40 μg of pure β-galactosidase (Boehringer, Mannheim, Germany) with admixture of 0.5 μg of synthetic MALP-2 or 10 μg of cholera toxin B subunit (CTB; ICN Biomedicals Inc., Ohio) as standard adjuvant. For intranasal administration (i.n.), 10 μl were administered into each nostril, while for the i.p. injection β-galactosidase was resuspended with or without MALP-2 in 400, 100 or 100 μl of PBS. Serum samples were taken at various times (day 0, 13, 20 and 30) and stored at −20° C. until the β-galactosidase-specific antibodies were determined. Nunc-Immuno MaxiSorp assay plates with 96 wells (Nunc, Roskilde, Denmark) were coated with 100 μl of β-gal (Boehringer, Mannheim, Germany) with 5 μg/ml in 0.05 M carbon buffer (pH 8.2) per well. Serial two-fold dilutions of the sera or lavages in PBS with 1% BSA and 0.05% Tween-20 were added (100 μl/well) and the plates were incubated at 37° C. for 24 hours. After rinsing, biotinylated γ chain-specific goat anti-mouse IgG (Sigma Chemie, Deisenhofen, Germany) was added, and the plates were incubated at 37° C. for a further hour. After rinsing four times, 100 μl of peroxidase-conjugated streptavidin (Pharmingen) were added to the cells, and the plates were incubated at 37° C. for 30 minutes. After rinsing four times, the reactions were developed by means of ABTS in 0.1 M citrate-phosphate buffer (pH 4.35) which contained 0.01% $H_2O_2$. The results have been shown as the reciprocal $log_2$ of the last dilution which, after incubation for 30 minutes, resulted in an optimal density at 405 nm of 0.1 units compared with the values for the negative control group.

On the basis of the encouraging results of the preliminary studies, we decided to analyze in detail the immune responses found on use of MALP-2 as adjuvant by the two most effective immunization routes, namely i.p. and i.n., and compare them with those for a proven mucosal adjuvant. Accordingly, the ability of MALP-2 to elicit an effective humoral immune response was assessed by determining the serum titer of β-galactosidase-specific antibodies in immunized mice. As shown in FIG. 6A, administration of pure β-galactosidase (50 μg/dose) resulted in induction of very low antibody titers, even after a second boost (endpoint titer about 1000). By comparison therewith, administration of β-galactosidase with use of MALP-2 i.n. induced, even with a single dose, to induction of very high titers (>60,000) of specific IgG in all the mice, and the titers at the end of the immunization protocol were above 500,000 (FIG. 6). The kinetics and the overall efficacy of the antibody responses achieved with 0.5 μg of MALP-2 were very similar to those achieved on administration of β-galactosidase with 10 μg of CTB, a proven mucosal adjuvant, which was used as positive control substance.

A marked adjuvant effect was also observed on i.p. administration of MALP-2. In particular, coinjection of MALP-2 led to a 100-fold increase in the β-galactosidase-specific IgG titers compared with the titers in animals immunized with pure β-galactosidase (FIG. 6B). This difference was to be found even after the first immunization and was maintained after booster injections. Similar antibody titers were found on day 31 in animals immunized either i.n. or i.p. However, the primary responses after MALP-2 coinjection were more pronounced after the i.n. immunization.

EXAMPLE 5: INTRANASAL COADMINISTRATION OF MALP-2 WITH A SOLUBLE ANTIGEN STIMULATES EFFECTIVE MUCOSAL ANTIBODY RESPONSES

Experimental Protocol:

The mice were sacrificed on day 31, and the final samples were taken. Vaginal and lung lavages were obtained by rinsing the organs with 1 ml of PBS supplemented by 50 mM EDTA, 0.1% BSA and 10 mM PMSF. The lavages were then centrifuged in order to remove tissue detritus (10 min at 3000×g) and the remaining liquid was stored at −20° C. In order to determine the total IgA concentration in the rinsings from lung and vagina, serial dilutions of the corresponding samples were incubated in microtiter plates, these plates having previously been coated with goat anti-mouse IgA (Sigma Chemie) as capture antibody (100 μl/well). Serial dilutions of purified mouse IgA (Sigma Chemie) were used to produce a standard plot.

In order to investigate the ability of MALP-2 to stimulate mucosal responses to antigens coadministered i.n., the production of β-galactosidase-specific IgA in lung and vaginal rinsings of immunized animals was. Whereas no production of β-galactosidase-specific IgA in detectable quantity in the lung rinsings took place after i.n. immunization with pure β-galactosidase, a significant increase in the level of antigen-specific IgA was found for the animals immunized with β-galactosidase and MALP-2 (FIG. 7). Coadministration of MALP-2 led to stimulation of an effective IgA production even in remote mucous membranes, and is demonstrated by the presence of significant concentrations of β-galactosidase-specific IgA in the vaginal rinsings (FIG. 7). No statistically significant differences were found in the levels of β-galactosidase-specific antibodies in the mucous membranes between animals immunized with 0.5 μg of MALP-2 or 10 g of CTB.

EXAMPLE 6: IMMUNIZATION WITH USE OF MALP-2 AS ADJUVANT DOES NOT LEAD TO MORE SERUM IGE

Experimental Protocol:

To determine the total IgE concentration in the serum of immunized and control animals, serial dilutions of the appropriate samples were incubated in microtiter plates which had previously been coated with anti-mouse IgE (100 μl/well) as capture antibody. After blocking with PBS with 1% BSA and 0.05% Tween-20 at room temperature for two hours, a 1:100 dilution of the serum in PBS-Tween was added (100 μl/well) and the plates were incubated at 37° C. for one hour. After rinsing, biotinylated anti-mouse IgE was added and the plates were incubated at 37° C. for a further hour. After rinsing four times, 100 μl of peroxidase-conjugated streptavidin (Pharmingen) were put in the wells, and the plates were incubated at 37° C. for 30 minutes. After rinsing four times, the reactions were developed by means of ABTS in 0.1 M citrate-phosphate buffer (pH 4.35) and a content of 0.01% $H_2O_2$. Serial dilutions of purified mouse IgE were used to produce a standard plot.

It is an acknowledged fact that the use of certain mucosal adjuvants may, because of an increase in IgE production, lead to allergic reactions. In order to check this hypothesis, we have started to examine the effect of MALP-2 administration on the serum IgE content. As is evident from FIG. 8, administration of MALP-2 by the parenteral (i.p.) route or via the mucous membranes does not lead to an increase in the serum IgE content. On the contrary, the presence of MALP-2 appears in fact to have a beneficial effect on the increase in the IgE content as observed on day 28 after i.p. immunization with pure β-galactosidase.

EXAMPLE 7: MALP-2 STIMULATES EFFICIENT T-CELL-MEDIATED PROLIFERATION RESPONSES WHEN IT IS ADMINISTERED TOGETHER WITH A SOLUBLE ANTIGEN

Experimental Protocol:

Lymph nodes located below the lower jaw and the spleens were removed and put together for the analysis of the cellular immune responses. The cells were grown in RPMI 1640 supplemented by 10% fetal calf serum, 10 U/ml penicillin, 50 µg/ml streptomycin, $5 \times 10^{-5}$ M 2-mercaptoethanol and 1 mM L-glutamine (GIBCO BRL, Karlsruhe, Germany) and stored at 37° C. in a moist atmosphere with 5% $CO_2$. The suspensions of lymph node and spleen cells were adjusted to $5 \times 10^6$ cells/ml in complete medium and put in a flat-bottomed 96-well microtiter plate (Nunc) with 100 µl/well, and the plates were incubated in the presence of various concentrations of soluble β-galactosidase for 4 days. Each concentration was tested in groups of three. During the last 18 hours of the incubation, 1 ρCi of [³H]thymidine (Amersham International, Freiburg, Germany) was added to each well. The cells were then harvested on filter paper (Filtermat A; Wallac, Freiburg, Germany) using a cell harvester (Inotech, Wohlen, Switzerland), and the amount of incorporated [³H]thymidine in the DNA of the proliferated cells was determined with the aid of a γ scintillation counter (Wallac 1450, Micro-Trilux). The results have been shown as the arithmetic mean of the uptake of [³H]thymidine in cpm.

The immune responses of T cells were investigated on day 31 by determining the proliferation of the cells obtained from regional lymph nodes and spleens after in vitro restimulation with β-galactosidase. The spleen cells from animals immunized i.p. with pure β-galactosidase were used as positive control group and showed a significant proliferation response compared with the unimmunized group (FIG. 9A). A further increase in proliferation was found in spleen cells derived from animals which had received coinjection of MALP-2 and antigen (p<0.05). Whereas i.n. administration of pure β-galactosidase caused no detectable cell proliferation, coadministration of MALP-2 led to an efficient proliferation response both in regional (lymph node cells) and in systemic (spleen cells) (FIGS. 9B and C). It is noteworthy that the greatest T-cell proliferation was observed for the spleen cells of mice to which MALP-2 and β-galactosidase had been administered i.n. (FIG. 9B). In all cases there was found to be a distinctly dose-dependent effect due to the increase in the β-galactosidase concentration during restimulation (5, 10, 20 µg/ml). Finally, use of MALP-2 (0.5 µg) as adjuvant led to a statistically significant (p<0.05) increase in T-cell proliferation compared with i.n. immunization with (10 µg) plus β-galactosidase (FIG. 8B).

EXAMPLE 8: ANALYSIS OF T-HELPER PATTERNS ELICITED THROUGH THE USE OF MALP-2 AS ADJUVANT

Experimental Protocol:

Nunc-immuno MaxiSorp assay plates with 96 wells (Nunc, Roskilde, Denmark) were coated with 100 µl of β-galactosidase (Boehringer, Mannheim, Germany) with 5 µg/ml in 0.05 M carbonate buffer (pH 8.2) per well. Serial two-fold dilutions of serum or rinsings in PBS with 1% BSA and 0.05% Tween 20 were added (100 µl/well), and the plates were incubated at 37° C. for 2 hours. After rinsing, biotin-conjugated rat anti-mouse IgG1, IgG2a, IgG2b, or IgG3 (Pharmingen, Hamburg, Germany) was added in order to determine the Ig subclasses. The plates were incubated at 37° C. for a further hour. After rinsing four times, 100 µl of peroxidase-conjugated streptavidin (Pharmingen) were added to the cells, and the plates were incubated at 37° C. for 30 minutes. After rinsing four times, the reactions were developed with ABTS in 0.1 M citrate-phosphate buffer (pH 4.35) which contained 0.01% $H_2O_2$. In order to determine the serum concentration of the IgG subclasses, standard plots were produced by coating the wells with an isotype-specific goat anti-mouse IgG and then incubating with purified mouse IgG1, IgG2a, IgG2b or IgG3 antibodies (Dianova, Hamburg, Germany).

Liquid supernatants from cultures of proliferating cells were removed on days 2 and 4 and stored at −70° C. Determination of IFN-γ, IL-2, IL-4 and IL-10 was carried out by means of an ELISA, using commercial antibodies from Pharmingen in accordance with the manufacturer's instructions. Briefly, 96-well microtiter plates were coated overnight with purified rat anti-mouse IFN-γ, anti-IL-2, anti-IL-4 or anti-IL-10 mAbs (Pharmingen) at 4° C. After three rinsings, the plates were blocked and the liquid supernatants were put in the wells. A standard plot was produced for each cytokine by using the corresponding recombinant rodent cytokines (Pharmingen). The plates were incubated at room temperature for a further 4 hours. After rinsing, biotinylated rat anti-mouse IFN-γ, IL-2, IL-4 or IL-10 mAbs (Pharmingen) was put in the wells, and the plates were incubated at room temperature for one hour. After rinsing six times, streptavidin-peroxidase conjugate was added and the plates were incubated at room temperature for 30 minutes. The plates were then developed with ABTS as described above.

Firstly, the subclass distribution of the β-galactosidase-specific IgG which was present in the serum of the immunized mice was. As shown in Table 1, the main type of β-galactosidase-specific IgI isotypes was IgG1, irrespective of the immunization protocol. This dominant Th2 response pattern was evident even after the first immunizing dose and was maintained during the following boosters. IgG1 was the only isotype found on administration of pure β-galactosidase, whereas coadministration with CTB or MALP-2 led to the finding of further β-galactosidase-specific isotypes, namely IgG2a (Typ Th1), IgG2b (Typ Th2) and IgG3 (Typ Th1). Despite this, the IgG1/2a (FIG. 10), IgG1/2b or IgG1/3 ratio remained above 100.

TABLE 1

β-Galactosidase-specific IgG isotypes
in the serum of immunized mice[a]

| Immunization group | IgG1 | IgG2a | IgG2b | IgG3 |
|---|---|---|---|---|
| β-gal (l.n.) | 22.6 +/− 21.3 | 0.7 +/− 0.5 | 0.3 +/− 0.1 | 0.6 +/− 0.0 |
| β-gal + MALP-2 (i.n.) | 6439.0 +/− 1775, | 20.8 +/− 5.4 | 43.3 +/− 18.9 | 2.4 +/− 0.5 |
| β-gal + CTB (i.n.) | 4108.3 +/− 1437, | 31.9 +/− 9.5 | 49.2 +/− 17.3 | 2.4 +/− 0.6 |
| β-gal (i.p.) | 191.5 +/− 132.1 | 0.1 +/− 0.0 | 0.5 +/− 0.1 | 0.6 +/− 0.0 |
| β-gal + MALP-2 (i.p.) | 2829.7 +/− 1119, | 10.0 +/− 2.8 | 15.8 +/− 6.2 | 2.3 +/− 0.6 |
| Control group | 0.4 +/− 0.0 | 0.23 +/− 0.0 | 0.1 +/− 0.0 | 0.4 +/− 0.0 |

[a]The results are shown as average (μg/ml) ± SEM (5 mice per group)

In order to characterize further the type of Th response elicited by the immunization, the IFN-γ, IL-2, IL-4 and IL-10 content was measured in the liquid supernatants from spleen cells stimulated in vitro (FIG. 11A). It was found that, of these four cytokines, IL-10 was most prominent, indicating that a Th2 response pattern had been generated. The IL-10 content was significantly higher in mice immunized i.n. with MALP-2 than in the control group (2.2 ng/ml compared with 0.009 ng/ml, p<0.005) and also by comparison with animals for which CTB had been used as mucosal adjuvant (0.6 ng/ml, p<0.05). The observed response pattern with a dominant cytokine of the Th2 type was consistent with the finding of β-galactosidase-specific IgG1 in the same animals (FIG. 10). In fact, the strong stimulation of IL-10 secretion is consistent with the part played by this cytokine in the inhibition of cytokine synthesis by Th1 cells, the improvement of B-cell proliferation and the stimulation of IgA production.

Despite the fact that the absolute levels of the cytokine concentration found in the cell culture media of cells obtained from regional lymph nodes were lower, the general pattern was the same as that found for spleen cell cultures (FIG. 10). It is of interest that although secretion of IL-10 and IL-4 was also stimulated in the cells from mice immunized i.p. with pure β-galactosidase, the Th1 cytokines IL-2 and IFN-γ remained below the limit of detection. In contrast thereto, IL-2 and IFN-γ were also found in the mice which had received the antigen mixed with CTB or MALP-2 (FIG. 10). These results are consistent with the IgG-isotype patterns found (Table 1) and confirm that although Th2 response types predominate, MALP-2 also assists stimulation of Th1 cells.

EXAMPLE 9: ORAL IMMUNIZATION WITH THE MODEL ANTIGEN β-GALACTOSIDASE WITH USE OF MALP-2 AS MUCOSAL ADJUVANT

Six- to eight-week old female BALB/c (H-2d) mice were purchased from Harlan Winkelmann GmbH (Borchen, Germany) and treated in accordance with local guidelines and directives of the European Community. Groups each of 5 mice were immunized on days 1, 14, 21 and 31 with 100 μg of β-gal (Boehringer, Mannheim, Germany) either alone or with 2 μg of synthetic MALP-2 as adjuvant by the oral route (dose 25 μl). On day 45, serum samples were taken and stored at −20° C. until β-gal-specific antibodies were determined. 96-well Nunc-Immuno MaxiSorp® assay plates (Nunc, Roskilde, Denmark) were coated with 100 μl of β-gal at 5 μg/ml in 0.05 M carbonate buffer (pH 8.2) per well. Serial two-fold dilutions of the sera or lavages in PBS with 1% BSA and 0.05% Tween 20 were added (100 μg/well), and the plates were incubated at 37° C. for 2 hours. After washing, biotinylated γ chain-specific goat anti-mouse IgG (Sigma Chemie, Deisenhofen, Germany) was added, and the plates were incubated at 37° C. for a further hour. After washing four times, 100 μl of peroxidase-conjugated streptavidin (Pharmingen) was added to the cells, and the plates were incubated at 37° C. for 30 minutes. After four washing steps, reactions were developed with ABTS in 0.1 M citrate-phosphate buffer (pH 4.35) which contained 0.01% $H_2O_2$. The final value titers have been expressed as the reciprocal logarithmic $\log_2$ values of the last dilution which resulted, after incubation for 30 minutes, in an optical density at 405 nm of 0.1 units above the values for the negative controls. Immune responses to β-gal were observed only in animals immunized with MALP-2 as mucosal adjuvant (see FIG. 12).

It is to be expected that the immune responses elicited also with different dosages both in the body fluids and in the cells will be more effective than those elicited on administration of the antigen alone. In addition, antigen-specific mucosal reactions are to be found at least locally in the intestines (i.e. the presence of antigen-specific secretory IgA in intestinal rinsings). It is additionally to be expected that secretory responses can be found in remote mucous membranes.

The invention claimed is:

1. A method of vaccinating an animal or human in need thereof, comprising the steps of:
providing said animal or human, via mucous membranes of said animal or human, with an antigen; and
providing said animal or human, via mucous membranes of said animal or human, with an adjuvant in the form of a lipopeptide or lipoprotein of the structure (I)

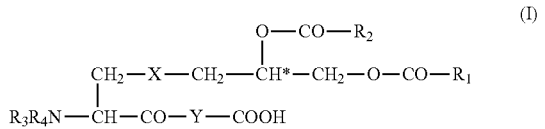

where
$R_1$ and $R_2$, which may be identical or different, are $C_{7-25}$-alkyl, $C_{7-25}$-alkenyl or $C_{7-25}$-alkynyl,
X is S, O or $CH_2$,
$R_3$ and $R_4$ are independently of one another H or methyl and
Y is a physiologically tolerated amino acid sequence which consists of 1 to 25 amino acid residues and is not immunogenic per se in the species used, and the asymmetric carbon atom marked with * as the absolute R configuration, according to the Cahn-Ingold-Prelog rule, when X is S (sulfur).

2. The method of claim 1, wherein the amino acid sequence Y is selected from a)
GQTNT (SEQ ID NO: 1)

b)
SKKKK (SEQ ID NO: 2)

c)
GNNDESNISFKEK (SEQ ID NO: 3)
and d)
GQTDNNSSQSAAPGSGTTNT. (SEQ ID NO: 4)

3. The method of claim 1, wherein the lipoprotein or lipopeptide of structure (I) is an S-[2,3-bispalmitoyloxy(2R) propyl]cysteinyl-peptide, where the peptide is a physiologically tolerated amino acid sequence which consists of 12 to 25 amino acid residues and is preferably not immunogenic in the species used.

4. The method of claim 1, wherein the adjuvant is present in a preparation with the antigen, and wherein said providing steps are performed simultaneously by an administration route selected from the group consisting of intranasal administration, intra-NALT administration, aerosolized oral administration, intrarectal administration, conjunctival administration, intravaginal administration, intraurethral administration, and administration into the milk ducts of the female breast.

5. The method of claim 1, wherein the adjuvant is present in a kit for coadministration with the antigen, and wherein each of said providing steps are performed by an administration route into the milk ducts of the female breast selected from the group consisting of intranasal, intra-NALT, aerosolized oral, intrarectal, conjunctival, intravaginal and intraurethral.

6. The method of claim 1, wherein said providing an animal or human with an adjuvant step simultaneously provides at least one further adjuvant or antigen.

7. The method of claim 1, wherein the lipopeptide or lipoprotein is associated or combined with a physical or biological carrier.

8. The method of claim 1, further comprising the step of providing, together with the lipopeptide or lipoprotein, one or more anti-inflammatory, antiangiogenic, cytotoxic or immunomodulatory substances, ligands or antibodies.

9. The method of claim 1, further comprising the step of providing the animal or human with further additives and excipients.

10. The method of claim 1, wherein the antigen is present in the form of peptides, proteins, DNA, polysaccharides, glycolipids or glucoproteins.

11. The method of claim 1, wherein Y consists of 12-25 amino acid residues.

* * * * *